(12) United States Patent
Lampman et al.

(10) Patent No.: US 6,889,073 B2
(45) Date of Patent: May 3, 2005

(54) BREAST BIOPSY AND THERAPY SYSTEM FOR MAGNETIC RESONANCE IMAGERS

(76) Inventors: David A. Lampman, 1413 Golden Gate Blvd., Mayfield Hts, OH (US) 44124; Nick Mastandrea, 1413 Golden Gate Blvd., Mayfield Hts, OH (US) 44124; Scott Thomason, 1413 Golden Gate Blvd., Mayfield Hts, OH (US) 44124

( * ) Notice: Subject to any disclaimer, the term of this patent is extended or adjusted under 35 U.S.C. 154(b) by 460 days.

(21) Appl. No.: 09/847,641

(22) Filed: May 2, 2001

(65) Prior Publication Data

US 2001/0039378 A1 Nov. 8, 2001

Related U.S. Application Data

(60) Provisional application No. 60/202,821, filed on May 8, 2000.

(51) Int. Cl.[7] ................................................ A61B 5/05
(52) U.S. Cl. ...................................... 600/422; 600/424
(58) Field of Search ............................... 600/422, 417, 600/410, 415, 423, 424, 426

(56) References Cited

U.S. PATENT DOCUMENTS

| | | | |
|---|---|---|---|
| 5,078,140 A | 1/1992 | Kwoh | 600/417 |
| 5,363,845 A | 11/1994 | Chowdhury | 600/422 |
| 5,437,280 A | 8/1995 | Hussman | 600/417 |
| 5,569,266 A | 10/1996 | Siczek | 600/130 |
| 5,602,557 A | 2/1997 | Duerr | 343/742 |
| 5,664,569 A | 9/1997 | Damadian | 600/421 |
| 5,678,549 A | 10/1997 | Heywang-Koebrunner | 600/417 |
| 5,682,890 A | 11/1997 | Kormos | 600/417 |
| 5,690,108 A | 11/1997 | Chakeres | 128/653.1 |
| 5,699,802 A | 12/1997 | Duerr | 600/422 |
| 5,706,812 A | 1/1998 | Strenk | 600/417 |
| 5,755,667 A | 5/1998 | Friedrich | 600/421 |
| 6,023,166 A | 2/2000 | Eydelman | 324/318 |
| 6,163,717 A | 12/2000 | Su et al. | 600/422 |
| 6,580,938 B1 * | 6/2003 | Acker | 600/424 |
| 6,589,163 B2 * | 7/2003 | Aizawa et al. | 600/118 |
| 6,591,130 B2 * | 7/2003 | Shahidi | 600/424 |
| 6,654,629 B2 * | 11/2003 | Montegrande | 600/424 |
| 6,731,966 B1 * | 5/2004 | Spigelman et al. | 600/407 |
| 6,773,393 B1 * | 8/2004 | Taniguchi et al. | 600/117 |

OTHER PUBLICATIONS

Katharina, C., et al., "Interventional Breast MR Imaging: Clinical Use of a Stereotactic Locialization and Biopsy Device", Radiology, 204: 669–675, 1997.

* cited by examiner

Primary Examiner—Daniel I. Robinson

(57) ABSTRACT

The present invention describes a device for performing breast biopsies and/or therapy within magnetic resonance imaging (MRI) systems. The apparatus includes a RF receiver antenna for magnetic resonance imaging of the breast. The RF coil includes openings in the front and side to provide access to the breast during the procedure. Compression plates are integrated into the breast coil which compress the breast either laterally or in the head/feet direction as required for optimal access to the breast. The apparatus includes a mechanical device for positioning interventional instruments in the breast such as biopsy or therapy instruments. The mechanical positioning devices position the instrument along the desired trajectory to the target site and insert the instrument into the breast while the patient remains inside the MRI scanner. Real time MR images may be acquired during instrument alignment and insertion to verify the trajectory. The mechanical positioning devices allow manipulation of instruments in any type of MRI scanner, including high field MRI systems with cylindrical magnets. The positioning devices provide a means to overcome limited access to the patient in MRI scanners. The positioning devices may be manually operated by means of gears, drive shafts, cables or other mechanical means. Or they may be electronically controlled by means of MR compatible motorized drive systems. The devices may be remotely controlled from outside the magnet for MRI systems that have limited access to the patient in the magnet. An interface between the electronically controlled drivers and the MRI scanner computer can provide robotic control of the instrument.

23 Claims, 5 Drawing Sheets

BREAST BIOPSY AND THERAPY SYSTEM FOR MAGNETIC RESONANCE IMAGERS

CROSS-REFERENCE TO RELATED APPLICATIONS

The enclosed patent application is based upon Provisional Application for Patent 60/202,821, filed on May 8, 2000.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention relates to MRI-guided breast biopsies and therapy. It describes an apparatus for performing breast biopsies and/or therapy inside any type of MRI scanner, including high field "closed" MRI systems. It includes a RF receive coil for magnetic resonance imaging (MR) of the breast and a mechanical device for positioning interventional instruments inside the MRI scanner. Real time MR imaging is used to guide and monitor the interventional procedure.

BACKGROUND OF THE INVENTION

Magnetic resonance imaging (MRI) is an important clinical modality for the detection and delineation of breast carcinoma. Its high sensitivity allows detection and characterization of breast lesions not seen by other imaging technologies. However, current MRI systems are not optimized for breast biopsy. Low field open MRI systems provide access to the patient but have limited imaging performance for detecting and characterizing breast carcinoma. High field "closed" systems provide superior imaging performance but have limited access to the patient, preventing the use of real time imaging to guide the biopsy.

Existing breast biopsy systems for high field closed MRI systems require that the patient be removed from the scanner in order to perform the biopsy. This prevents the use of real time imaging to guide the biopsy. Errors in the instrument trajectory cannot be detected which can reduce the diagnostic quality of the tissue sample.

U.S. Pat. No. 6,163,717 issued in the name of Su, discloses an open breast coil for interventional MRI. Su does not disclose methods for incorporating breast compression plates into the coil or a means to position breast biopsy or therapy instruments inside the MRI scanner. Su's design is most useful for a lateral access to the breast. Access from the front is more limited than the present invention. Also, Su's design does not teach a robust means of supporting the patient weight while maintaining adequate access to the breast for performing interventional procedures.

U.S. Pat. No. 5,706,812, granted to Strenk, teaches a MRI breast biopsy coil with a transverse access portal and a stereotactic flame for guiding a biopsy needle. The coil is a linear coil that has reduced sensitivity compared to quadrature or phased array imaging coils. The design does not allow breast compression laterally or in the head/feet direction. Also, the design does not teach means for positioning instruments in the MRI scanner or methods of performing breast biopsies inside high field MRI scanners with limited access to the patient.

U.S. Pat. No. 5,755,667, issued in the name of Friedrich, discloses a MRI breast coil with compression plates. The coil is not open and does not allow performance of breast biopsies while the patient remains inside the MRI scanner.

U.S. Pat. No. 5,437,280, issued to Hussman, teaches a localizer apparatus suitable for guidance of medical instruments to lesions in the breast using a MR visible coordinate system. The patent does not teach design of open breast imaging coils or methods of performing breast biopsies while the patient remains inside the MRI scanner.

U.S. Pat. No. 5,678,549, granted to Heywang-Koebrunner, discloses a stereotactic compression device and imaging coil for performing MRI guided breast biopsies. The patent does not disclose breast coil designs that are open in the front, or a means of performing breast biopsies inside high field MRI systems. The device requires that the patient be removed from the scanner to perform the biopsy.

U.S. Pat. No. 5,690,108, issued to Chakeres, teaches an apparatus for aligning an instrument along a desired trajectory to a target using MR imaging. It does not teach open access imaging coils for breast biopsy or a method to insert a variety of instruments into the patient inside the MRI scanner.

U.S. Pat. No. 5,569,266, granted to Siczek, discloses a MRI guided breast biopsy device, including an imaging coil and a device for positioning a biopsy instrument in the breast. The patent does not disclose means to insert instruments into the patient while they remain inside the scanner. The device requires that the patient be removed from the scanner to insert the biopsy instrument.

SUMMARY OF THE INVENTION

To overcome the limitations of the known apparatus and medical procedures we have discovered a novel apparatus that provides important advantages over the prior art. The subsequently disclosed and claimed invention discloses a device for performing MRI guided breast biopsies and/or therapy without having to remove the patient from the scanner. The device can be used in any type of MRI system, including both low field open MRI systems and high field "closed" systems. The device allows a variety of interventional procedures to be performed on the breast using real time MR for guidance and monitoring.

According to one aspect of the present invention, the MRI biopsy device includes a RF receiver coil for imaging both breasts, said coil being open in the front and the side in order to provide access to the breast while the patient remains inside the scanner. The patient lies prone on top of the coil and the breasts extend down into the coils. In high field closed scanners the patient is put feet first into the cylindrical magnet and the procedure is performed from the front of the magnet through the opening in the front of the coil. Alternatively, the patient may be put into the scanner head first and the procedure is performed from the rear of the magnet through the opening in the front of the coil.

According to another aspect of the invention, the breast coil includes compression plates for compressing the breast during imaging and holding it rigidly in place during the biopsy or therapy. The compression plates are designed such that they may compress the breast in either the head/feet direction or laterally. The compression plates include holes through which the interventional instrument is inserted into the breast. In one embodiment the compression plate includes a grid of finely-spaced holes through which the instrument is inserted. In another embodiment the compression plate includes large rectangular access windows through which the instrument is inserted.

According to a further aspect of the present invention, the device includes a mechanical apparatus for positioning an instrument inside the MRI system. In the preferred embodiment an instrument is attached to the mechanical positioning apparatus and the position of the instrument is manipulated by a plurality of mechanical means. The controls for the mechanical instrument positioning device may be substantially removed from the instrument positioning assembly, providing remote control of the instrument position. Remote control operation is especially advantageous in the cylindrical magnets of high field "closed" MRI systems. Mechanical means for positioning the instrument inside the MRI scanner allows the use of real time imaging to guide the alignment of the trajectory and the insertion of the instrument into the lesion.

Alternate embodiments include positioning thermal therapy or drug delivery probes inside the MRI system, using real-time imaging to guide and/or monitor the procedure. Another embodiment includes remote control operation of interventional instruments inside the MRI scanner and robotic control of the instrument position.

DESCRIPTION OF THE DRAWINGS

FIG. 1 also shows the compression plates used to secure the breast in the coil.

DETAILED DESCRIPTION OF THE INVENTION

Figure 1A:
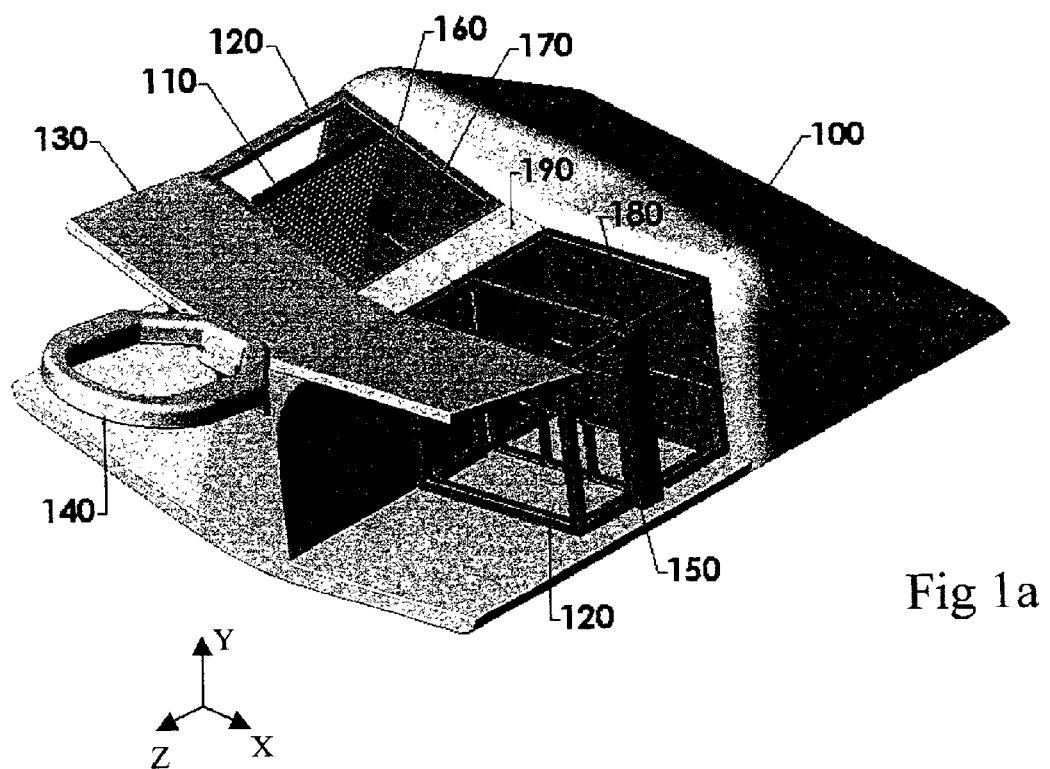
FIG. 1 is a view of the bilateral breast receiver coil with open access from the front and lateral directions.

FIG. 1 shows the breast imaging coil assembly. The patient lies prone on top of the coil with the sternum resting on the central support beam 190. The patient's head is supported by head support 140. The patient's shoulders are supported by shoulder supports 130. The patient's breasts extend down into the RF coil assemblies 120. In a high field closed MRI scanner the patient may be inserted feet first into the cylindrical magnet and the procedure performed from the front of the magnet through the opening in the front of the coil. Alternatively, the patient may be put into the scanner head first and the procedure performed from the rear of the magnet through the open in the front of the coil.

The breasts are compressed by compression plates 110 or 150. Said compression plates may compress the breast either in the head/feet direction (z axis) or the lateral direction (x axis). The compression plates may be one of two types; compression plate 110 consists of a plastic plate with a grid of finely-spaced needle guide holes. In FIG. 1 the compression plate 110 is shown oriented along the lateral direction but it may also compress the breast in the head/feet direction. Compression plate 150 consists of a plastic plate with large rectangular access windows, which is advantageous when a mechanical device is used for positioning the interventional instrument, as is described below. Compression plate 150 can be made MR visible by embedding or attaching MR visible material such as tubes filled with water to said compression plate. FIG. 1 shows compression plate 150 compressing the breast in the head/feet direction but it may also be used in the lateral direction.

Figure 1B:
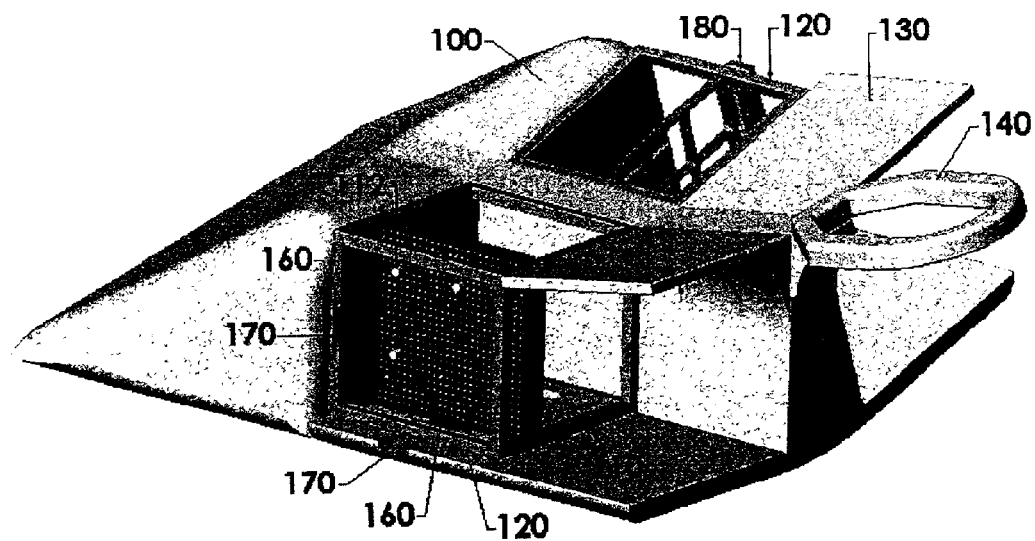

Referring to FIG. 1b, the compression plates are secured to the breast coil housing by means of clamps or latching mechanism 160 which slide in and out of the coil housing by means of side rails 170 embedded in the coil housing. The compression plates may also be secured to the coil cross-members 120 by means of clamps or latch mechanism 180.

Compression plate 110 includes MR visible markers 112. The position of the markers 112 relative to the tumor is measured on the MR images. The proper needle entry hole is then determined by determining which hole in the compression plate is closest to the desired entry point, as is known in the art (see for example U.S. Pat. Nos. 5,678,549 and 5,437,280).

Compression plates 110 and 150 may also be used for laterally directed biopsies performed outside the magnet as is known in the art (see for example Katharina, et al., Radiology, 1997; 204: 667–675).

The housing for the coil also includes an abdominal support (100), and head and shoulder supports (130, 140). The head support 140 and shoulder supports 130 may be elevated at an angle in order to provide additional access to the breast from the front.

Figure 2:
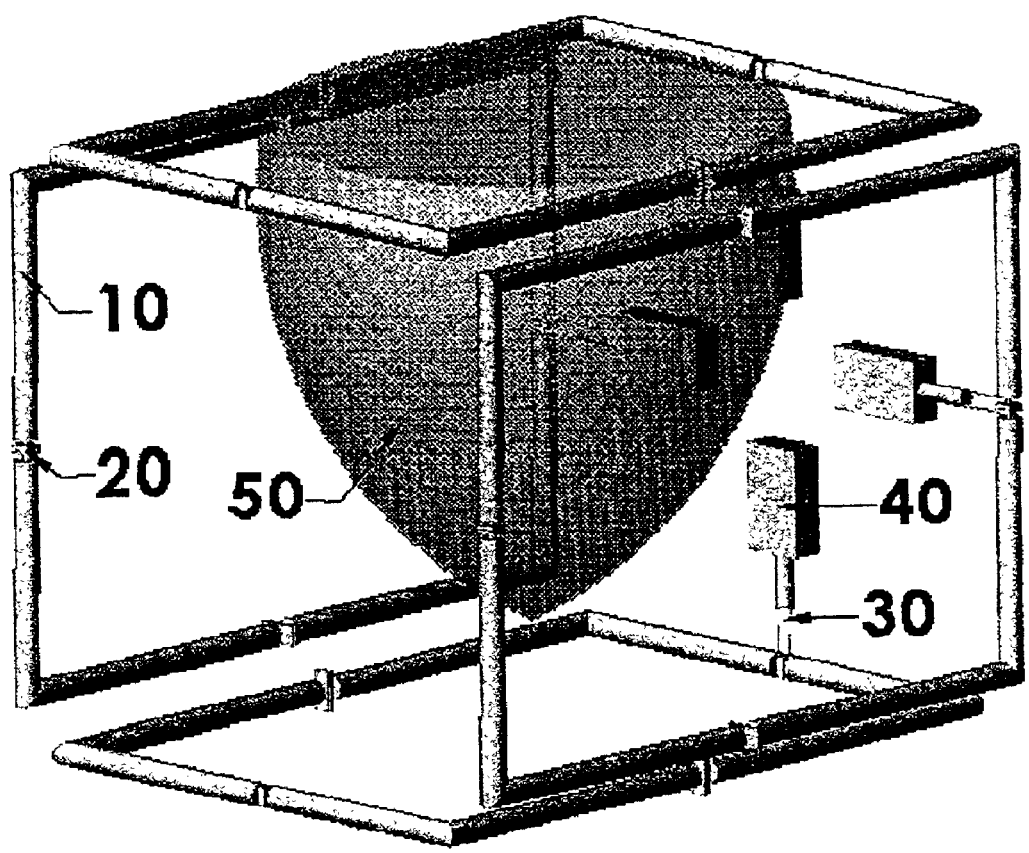
FIG. 2 shows the conductor geometry for the RF antennae in the bilateral breast receiver coil.

FIG. 2 shows a schematic view of the RF antennas that are enclosed in the breast receiver coils 120. The RF antenna conductor elements 10 are configured to form four loop antennae spaced apart vertically and horizontally sufficiently to accommodate the patient's breast 50. The RF antenna housings are open in both the lateral and front (head) directions, as shown in FIG. 1. This provides access to the breast either from the front or the side. The patient's breasts are inserted through the top opening in the coils. The RF signals from each of the coils are conducted into an electronic interface 40 by means of cables 30. The coils may be electrically combined as a quadrature coil or as a 4-channel phased array coil. The RF signals from each of the coils are pre-amplified and combined as required in the electronic interface(s) 40, as is known in the art. The capacitors 20 are used to time the coil to the proper operating frequency of the MRI scanner and to suppress unwanted eddy currents in the RF coils. Additional capacitors not shown in the electronic interfaces 40 are also used for tuning the coil to the proper operating frequency and impedance matching.

FIG. 2 shows the embodiment of the coil geometry for a high field MRI system with the magnetic field oriented along the z-axis. In low field "open" MRI systems the magnetic field is oriented along the y-axis. For this case, the coil assembly shown in FIG. 2 is rotated 90 degrees about the x-axis in order to maintain the proper orientation of the coil with respect to the direction of the magnetic field. The coil housing and compression plates require no modifications for this embodiment.

In an alternate embodiment the coil may consist of only 2 antennae, spaced apart either vertically or horizontally. This embodiment could provide improved access to the patient at the expense of imaging sensitivity.

Figure 3A:
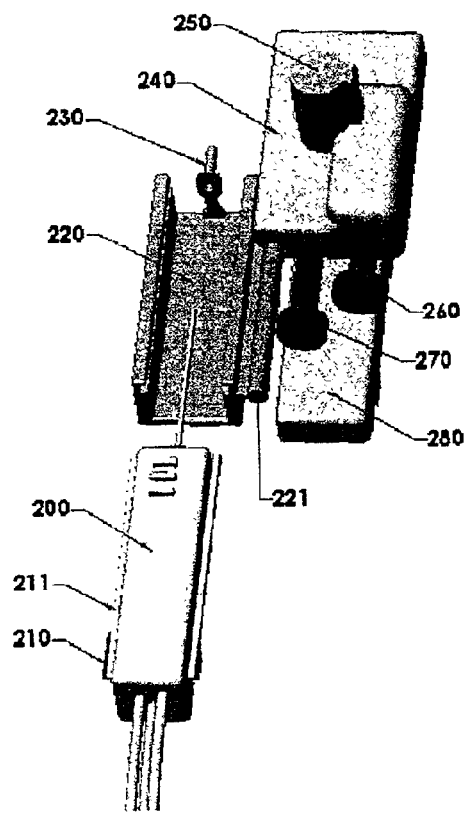
FIG. 3 shows the mechanical positioning device that is used to position an interventional instrument such as a biopsy needle or therapy probe in the MRI scanner.
Figure 3B:
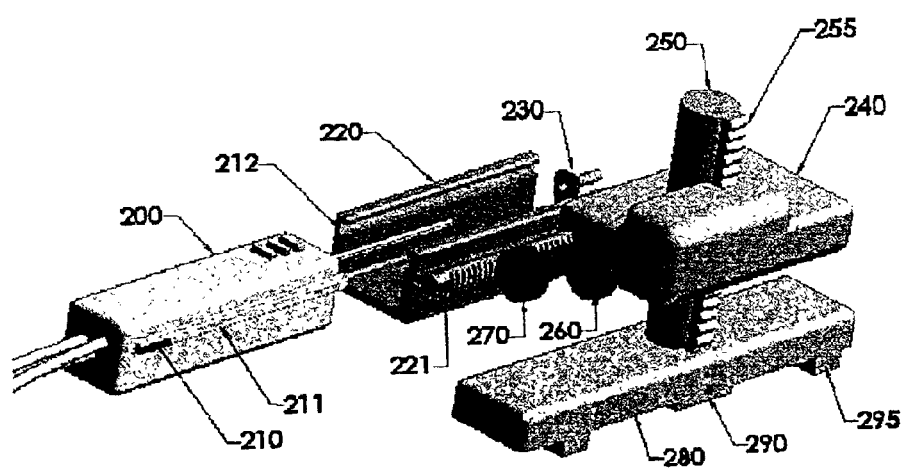

FIG. 3 shows a manually operated mechanical apparatus for positioning instruments within the MRI scanner. The instrument 200 can be any one of a number of commercially available biopsy instruments. Alternatively, the instrument could be a therapy probe such as a RF, laser or cryogenic probe for thermal ablation of tumors or a drug delivery probe for localized delivery of drugs. In the embodiment shown in FIG. 3 the interventional instrument 200 is mounted to the instrument platform 220 by means of side rails 211 on said instrument 200 that slide into corresponding slots 212 on instrument platform 220 (see FIG. 3b). The instrument 200 may be rigidly secured to the instrument platform 220 by means of snaps 210 on said instrument. Said snaps mate with corresponding indentations in the instrument platform 220. An alternate embodiment uses clamps to secure the instrument 200 to the instrument platform 220. The instrument platform 220 includes a MR-visible needle guide 230 that is visible in the MR images, providing a means to align the instrument trajectory using real time MR imaging, as described below. The MR visible needle guide 230 consists of a cylinder with an inner cavity filled with MR visible material such as water, Gd-DPTA, or vegetable oil. Instrument platform 220 is attached to mounting block 240 by means of an inchworm gear 221. By rotating drive shaft 270 the inchworm gear 221 advances the instrument platform 220 such that the instrument 200 is advanced into the patient. In an alternate embodiment, the instrument may be manually inserted through the needle guide into the patient. Mounting block 240 is also used to control the vertical motion of the instrument platform. A rack 255 is attached to vertical support post 250 (FIG. 3b). A corresponding pinion gear in mounting block 240 (not shown) is used to drive the mounting block up and down the vertical support post 250. Drive shaft 260 on mounting block 240 is used to drive the pinion gear in said mounting block. The base-plate 280 of the instrument positioning device includes guide rails 295 and a threaded borehole 290.

Figure 4:
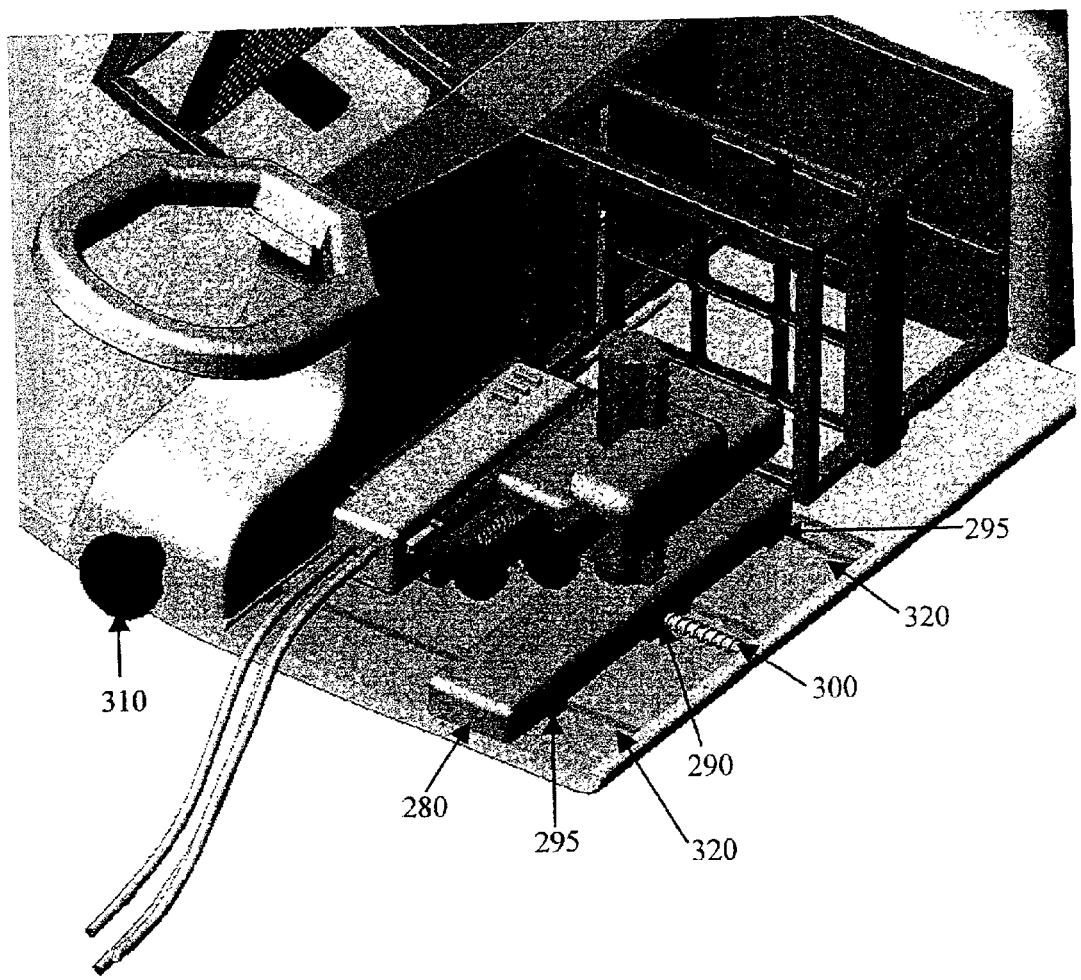
FIG. 4 shows the mechanical positioning device integrated into the breast coil assembly.

With reference to FIG. 4, the mechanical positioning device is mounted to the base of the breast-imaging coil. Base-plate 280 is attached to an acme screw 300 in the base of the imaging coil by means of threaded bore hole 290 through said base-plate. Acme screw 300 is used to move the base-plate 280 of the instrument positioning device in the left/right direction. In this manner rotational motion of said acme screw translates into linear motion of said base-plate. Drive shaft 310 is used to rotate the acme screw. Rails 295 in baseplate 280 travel along guide slots 320 in the base of the breast coil. Said rails and slots serve to guide base-plate 280 along the guide slots 320 and prevent twisting or rotation of the base-plate assembly.

Figure 5:
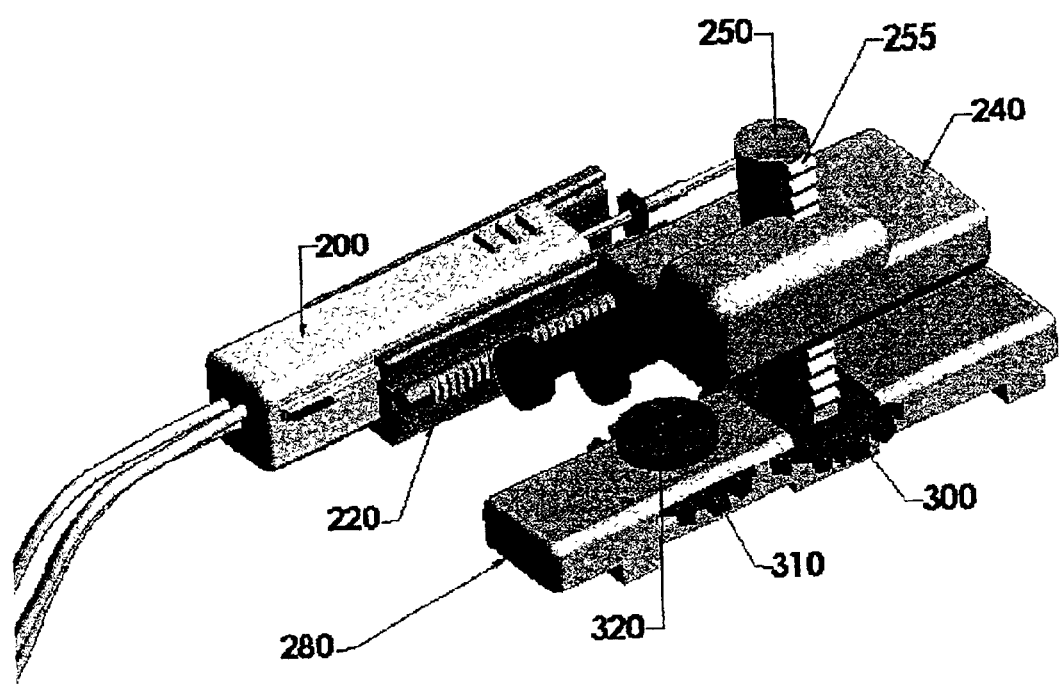
FIG. 5 shows a mechanical positioning device with a regional degree of freedom about the Y-axis.

FIG. 5 shows a mechanical positioning device with a rotational degree of freedom about the y-axis. This device enables the use of oblique trajectories to the target. Support post 250 is mounted on a rotatable gear 300. Gear 300 is rotated by a second gear 310. Gear 310 is rotated by means of drive shaft 320.

The desired trajectory to the target is determined from a preliminary set of MR images. There are a number of methods that can be used to align the trajectory of the instrument. In the simplest embodiment the needle guide 230 is aligned with the desired trajectory by acquiring real time MR images in the plane of said trajectory and adjusting the position of said needle guide so that it is aligned with the desired trajectory in the MR images. In an alternate embodiment, real time MR images may be acquired in a plane perpendicular to the desired trajectory with the center of the imaging plane centered on the line defining the trajectory. The imaging plane is offset so that a cross sectional image of needle guide 230 is visible in the images. The position of the needle guide is then adjusted until the cross section of the needle guide is aligned with the desired trajectory in the images. Following trajectory alignment the instrument is inserted into the patient through said needle guide. Real time images are acquired in the plane of the instrument to verify that the instrument insertion trajectory is correct. Realignment of the instrument trajectory may be performed in real time based on feedback from the MR images. In this manner, misalignment in the trajectory or any other sources of error in the instrument position may be detected and compensated for in real time.

In high-field "closed" MRI systems the preferred embodiment is to locate the instrument positioning device in the front of the coil, thereby providing a means to insert the instrument from the direction of the patient's head. A lateral approach in a high field system is limited by the diameter of the magnet bore. In a low field "open" ME system the instrument positioning device may be located either in the front or the side of the coil, providing a means to insert the instrument either from the front or lateral directions.

A plurality of positioning devices may be used to insert a plurality of instruments into one or both breasts in a single session. For example, two positioning devices could be used to insert instruments into both breasts, either from the front or the side. In another embodiment, a positioning device could be located in front of the coil and a separate positioning device could be located on the side of the coil, providing a means to insert instruments both from the head and lateral directions. In a low field open MRI system up to four positioning devices could be used in a particular session, two in the front and one on each side of the patient.

The mechanical positioning device must not distort the magnetic field of the MRI scanner so all of its components must be non-ferrous. Also, the positioning device must not interfere with the RF and pulsed magnetic field gradients of the MRI system so the use of conductive components must be avoided. Preferred materials for construction of the positioning device include thermo-plastics and thermo-sets.

In an alternate embodiment, an inchworm gear may be used for vertical motion of the instrument platform. A rack and pinion drive mechanism may also be used for horizontal motion of the instrument platform.

Another alternate embodiment uses cables instead of drive shafts to move the positioning device. The cables may be used to rotate the gears which move the instrument platform, mounting block, base-plate and/or support post. Alternatively, the cables may be directly connected to the instrument platform, mounting block and/or base-plate. The cables would then apply a push/pull to these components, causing them to move along guide rails, guide slots and/or guide rods.

In another alternate embodiment the positioning device may be used to position other types of instruments, such as spring-loaded biopsy guns, thermal therapy probes, or drug delivery probes. The instrument platform 220 may be modified as required to accommodate instruments of a variety of shapes and sizes. Alternatively, a variety of adaptors could be designed to mate a variety of instruments to the instrument platform 220 shown in FIG. 3.

Another alternate embodiment is to electronically control the position device by means of MR compatible motors. Examples of MR compatible motors include piezoelectric motors, vacuum-actuated drivers or hydraulic drivers. Electronic control of the mechanical positioning device allows remote control operation of the instrument inside the MRI scanner. Robotic control of the instrument is accomplished by means of an interface such that the MRI scanner computer controls the motors that drive the instrument positioning device.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A MR compatible mechanical device for positioning an interventional instrument such as a biopsy needle or therapy probe inside a MRI scanner, said positioning device comprising;

an instrument platform in which a biopsy or therapy instrument is secured to a mechanical positioning device, said platform being movable to align the instrument trajectory, insert the instrument to the patient and remove the instrument from the patient.

a mounting block to control the vertical and horizontal motion of the instrument platform, said mounting block including or attached to a mechanical means for horizontal motion of the instrument platform and another mechanical means for vertical motion of the instrument platform.

a base-plate that is attached to a mechanical means that moves said base-plate in a horizontal or vertical direction, a single post or a plurality of posts that support the aforementioned mounting block and physically link said mounting block to the aforementioned base-plate, said support post(s) attached to a mechanical means for moving said mounting block, a plurality of mechanical means for adjusting the position of the aforementioned instrument platform, mounting block and base-plate.

2. The apparatus of claim 1, further comprising a means of mounting the positioning device to said imaging coil.

3. The apparatus of claim 1, whereby the positioning device is located in front of the coil, providing a means to insert instruments into the patient from the direction of the patient's head.

4. The apparatus of claim 1, whereby the positioning device is located on the side of the coil, providing a means to insert intents into the patient from the lateral direction.

5. The apparatus of claim 1, further comprising a plurality of positioning devices that can be used to position a plurality of instruments in one or both breasts.

6. The apparatus of claim 1, further comprising an acme screw for moving the base-plate along a horizontal or vertical axis.

7. The apparatus of claim 1, further comprising an inchworm gear for moving the instrument platform along a horizontal or vertical axis.

8. The apparatus of claim 1, further comprising a rack and pinion mechanism for moving the instrument platform along a horizontal or vertical axis.

9. The apparatus of claim 1, further comprising a mechanical means of rotating the support post about an axis.

10. The apparatus of claim 9, further comprising a plurality of gears for rotating the support post about an axis.

11. The apparatus of claim 1, further comprising manually operated drive shafts and gears to adjust the position of the instrument platform inside the MRI scanner.

12. The apparatus of claim 1, further comprising cables to adjust the position of the instrument platform.

13. The apparatus of claim 1, further comprising an instrument platform with side rails for guiding an instrument along a predetermined trajectory.

14. The apparatus of claim 1, further comprising an instrument platform with indentations or clamps to secure the instrument into a locked position in the instrument platform.

15. The apparatus of claim 1, further comprising a needle guide for guiding the needle along a predetermined trajectory.

16. The apparatus of claim 1, further comprising a needle guide containing MR visible material for trajectory alignment of an instrument by means of MR imaging.

17. The apparatus of claim 16, further comprising a method for aligning the trajectory of an instrument and verifying the insertion trajectory of an instrument in a MRI scanner using real time MR imaging, said trajectory imaging method comprising;

selecting a desired trajectory to a lesion from a set of MR images, acquiring a time series of real time MR images in the plane of the desired trajectory to the target, adjusting the position of the MR visible needle guide until it appears in the images aligned with the desired trajectory to the target, inserting the instrument into the patient along the trajectory indicated by said needle guide, acquiring real time MR images in the plane of the instrument as it is inserted to verify that the trajectory conforms to the desired trajectory, interactively adjusting the insertion trajectory of the instrument to maintain a correct course using real time MR images for feedback.

18. The apparatus of claim 16, further comprising a method for aligning the trajectory of an instrument and verifying the insertion trajectory of an instrument in a MRI scanner using real time MR imaging, said trajectory imaging method comprising;

selecting a desired trajectory to a lesion from a set of MR images, acquiring a series of real time MR images perpendicular to the plane of the desired trajectory, said imaging plane centered on the desired trajectory to the target and offset to include a cross-section of the MR visible needle guide, adjusting the position of the MR visible needle guide until the cross sectional image of the needle guide indicates that said needle guide is aligned with the desired trajectory to the target, inserting the instrument into the patient along the trajectory indicated by said needle guide, acquiring real time MR images in the plane of the instrument as it is inserted into the patient to verify that the trajectory conforms to the desired trajectory, interactively adjusting the insertion trajectory of the instrument to maintain a correct course using real time MR images for feedback.

19. The apparatus of claim 16, further comprising a means to manually insert the instrument along the trajectory indicated by said needle guide.

20. The apparatus of claim 1, further comprising an instrument platform for positioning therapy instruments, such as RF, laser, cryogenic or drug delivery probes, inside a patient in a MRI system using real time imaging for guidance and monitoring of the therapy.

21. The apparatus of claim 1, further comprising a remotely controlled means for adjusting the position of the instrument inside the MRI scanner.

22. The apparatus of claim 1, further comprising an electronically controlled means for adjusting the position of the instrument inside the MRI scanner.

23. The apparatus of claim 22, further comprising a robotically controlled means for adjusting the position of the instrument inside the MRI scanner.

* * * * *